United States Patent
Park et al.

(10) Patent No.: US 7,777,090 B2
(45) Date of Patent: Aug. 17, 2010

(54) POLYURETHANE FOAM DRESSING FOR WOUND FILLER AND METHOD FOR MANUFACTURING THEREOF

(75) Inventors: Myung-Hwan Park, Seoul (KR); Soo-Chang Lee, Seoul (KR); Sun-Ae Kang, Anyang (KR)

(73) Assignee: Biopol Co., Ltd., Kyunggi-do (KR)

( * ) Notice: Subject to any disclaimer, the term of this patent is extended or adjusted under 35 U.S.C. 154(b) by 823 days.

(21) Appl. No.: 10/533,123

(22) PCT Filed: Oct. 23, 2003

(86) PCT No.: PCT/KR03/02242

§ 371 (c)(1),
(2), (4) Date: Feb. 16, 2007

(87) PCT Pub. No.: WO2004/039421

PCT Pub. Date: May 13, 2004

(65) Prior Publication Data

US 2009/0069736 A1    Mar. 12, 2009

(30) Foreign Application Priority Data

Oct. 29, 2002  (KR)  ................. 10-2002-0066191

(51) Int. Cl.
*A61F 15/00* (2006.01)
(52) U.S. Cl. .......................... 602/42; 602/46
(58) Field of Classification Search ............. 602/41–54
See application file for complete search history.

(56) References Cited

U.S. PATENT DOCUMENTS

| 3,800,792 | A | 4/1974 | McKnight et al. |
| 3,978,855 | A | 9/1976 | McRae et al. |
| 4,538,603 | A | 9/1985 | Pawelchak et al. |
| 4,664,662 | A | 5/1987 | Webster |
| 4,704,113 | A | 11/1987 | Schoots |
| 5,064,653 | A | 11/1991 | Sessions et al. |
| 5,065,752 | A | 11/1991 | Sessions et al. |
| 5,254,301 | A | 10/1993 | Sessions et al. |

(Continued)

FOREIGN PATENT DOCUMENTS

EP    0 335 669 A    10/1989

(Continued)

OTHER PUBLICATIONS

Park et al. (2002) J Korean Soc. Plast. Reconstr. Sur. 29(4):297-301 Medifoam® (Hydropholic Polyurethane Foam).

(Continued)

*Primary Examiner*—Michael A. Brown
(74) *Attorney, Agent, or Firm*—Swanson & Bratschun, L.L.C.

(57) ABSTRACT

A polyurethane foam dressing for a wound filler, which includes a hydrophilic polyurethane foam including a plurality of open cells with a diameter of 50 to 400 μm and a plurality of pores with a diameter of 10 to 80 μm, and a method of manufacturing the same including mixing and agitating 40 to 75 wt % pre-polymer, 15 to 45 wt % foaming agent, 5 to 35 wt % crosslinking agent, and 0.5 to 15 wt % additive containing a surfactant, a moisturizing agent, and a pigment, injecting the resulting mixture into a mold, and foaming the resulting mixture injected into the mold.

2 Claims, 1 Drawing Sheet

U.S. PATENT DOCUMENTS

| | | | |
|---|---|---|---|
| 5,445,604 A | 8/1995 | Lang | |
| 5,489,262 A | 2/1996 | Cartmell et al. | |
| 5,501,661 A | 3/1996 | Cartmell et al. | |
| 5,503,847 A | 4/1996 | Queen et al. | |
| 5,571,529 A | 11/1996 | Cheong | |
| 5,830,932 A | 11/1998 | Kay | |
| 6,207,875 B1 | 3/2001 | Lindqvist et al. | |
| 6,326,410 B1 | 12/2001 | Cheong | |
| 6,486,378 B1 | 11/2002 | Areskoug et al. | |
| 6,881,875 B2 | 4/2005 | Swenson | |
| 2002/0062097 A1* | 5/2002 | Simpson | 602/46 |
| 2004/0018227 A1 | 1/2004 | Park et al. | |
| 2008/0146983 A1 | 6/2008 | Park et al. | |

FOREIGN PATENT DOCUMENTS

| | | |
|---|---|---|
| EP | 00335669 | 10/1989 |
| GB | 2 290 031 A | 12/1995 |
| KR | 2001008533 A * | 2/2001 |
| KR | 1020010008533 A | 2/2001 |
| KR | 2002-0046619 A | 6/2002 |
| KR | 340981 B | 6/2002 |
| KR | 1020020046619 A | 6/2002 |
| KR | 553078 | 6/2005 |
| WO | WO 00/78369 A1 | 12/2000 |

OTHER PUBLICATIONS

Lim et al. (2003) J Korean Burn Soc. 6(1):45-51 Foam Dressing Material.

Office Action issued Jan. 8, 2009 in U.S. Appl. No. 11/627,651.

Office Action issued Jul. 1, 2009 in U.S. Appl. No. 11/627,651.

Office Action issued Nov. 2, 2009 in U.S. Appl. No. 11/627,651.

International Search Report issued Jan. 25, 2005 in corresponding PCT application serial No. PCT/KR2003/002242.

International Preliminary Examination Report issued Jan. 29, 2005 in corresponding PCT application serial No. PCT/KR2003/002242.

* cited by examiner

POLYURETHANE FOAM DRESSING FOR WOUND FILLER AND METHOD FOR MANUFACTURING THEREOF

The present invention claims the benefit of Korean Patent Application No. 10-2002-0066191, filed in Korea on Oct. 29, 2002, and International Application No. PCT/KR2003/002242, filed on Oct. 23, 2003, which are all hereby incorporated by reference.

TECHNICAL FIELD

The present invention pertains, in general, to a polyurethane foam dressing for a wound filler, which is used to support the healing of a deep wound and, more particularly, to a polyurethane foam dressing for a wound filler, which includes a hydrophilic foam containing a plurality of open cells with a diameter of 50 to 400 μm and a plurality of pores with a diameter of 10 to 80 μm, and a method of manufacturing the same. Additionally, the polyurethane foam dressing is characterized in that it has high absorptivity of 500 to 2000 wt % and high moisture vapor transmission rate of 2000 to 5000 g/m/$^2$/24 hrs at 35° C. and a relative humidity of 90%, and rapidly absorbs an exudate from the wound.

BACKGROUND ART

The skin is an organ that performs a variety of significant biological functions, such as protecting internal tissues from external threats, regulation of a body temperature, preventing viral invasions, perception, and secretion. Destruction of the skin by a trauma, a wound, a burn, or a decubitus can cause loss of these protective functions, making a patient experience discomfort until a wound is healed, and in some cases that the skin is extensively damaged, the patient's life is endangered.

Particularly, in the case of the decubitus or open surgical wound, a large quantity of secretion is oozed from a wounded portion of the skin, thus it is necessary to prevent the secretion from stagnating on the wound to suppress the infection of the skin. If blood or exudate oozed from the wound such as pustule stagnates on the wound, the propagation of bacteria occurs which infects the skin to delay the healing of the wounded skin. Additionally, the exudate may lead to the maceration of tissues around the wound to enlarge a wounded portion of the skin. Nevertheless, the dryness of a surface of the wound caused by the excessive removal of the exudate is not preferable because moisture is needed in order to efficiently heal the wounded skin.

Additionally, a dressing capable of maintaining the wound under a humid environment, being freely deformed according to a shape of the wound, and having excellent exudate absorptivity is useful to support the healing of the wound such as a cavity, a pocket, or a decubitus, from which a large amount of exudate is oozed. The term "excellent exudate absorptivity" denotes an ability that the dressing rapidly absorbs the exudate in large amount. In the case of a gauze dressing for a wound filler used to support the healing of a deep wound, an absorption rate of the exudate into the gauze dressing is relatively fast, but the absorptivity of the exudate into the gauze dressing is relatively low. Further, the gauze dressing serves to maintain the wound under a dry environment to delay the healing of the wound, and the replacement of the gauze dressing is not easily conducted and causes the damage of a regenerated tissue and the discomfort of a patient because the gauze dressing is attached to the wound under the dry environment. Additionally, the gauze dressing is disadvantageous in that the gauze dressing must be replaced often at an initial healing step of the wound because a large amount of the exudate is oozed from the wound. Some improved dressings have been developed to avoid disadvantages of the gauze dressing, but have disadvantages in that their absorptivity and moisture vapor transmission rate are poor, they are not freely filled in the wound, and when they are separated from the wound to replace them, portions of the dressings remain on the wound because they are firmly attached to the surface of the wound.

Examples of the above improved dressings include an alginate dressing, a hydrocolloid dressing, a hydrogel dressing, and a polyurethane foam dressing.

U.S. Pat. No. 4,704,113 discloses a hydrophilic alginate dressing with 10 to 20 times absorptivity its weight, which is useful to support the healing of a deep wound oozing a large amount of exudate because when a portion of the alginate dressing remains on the wound, such a portion can be removed using a saline solution. However, this patent is disadvantageous in that when the used alginate dressing is replaced with a new one, a viscous material may remain on the wound, and the alginate dressing is firmly attached to the wound under a dry environment to damage a regenerated tissue when the alginate dressing is removed from the wound.

Additionally, U.S. Pat. Nos. 5,503,847 and 5,830,932 suggest a hydrocolloid dressing including an attachable composition layer, a hydrocolloid layer relieving an external impact and absorbing an exudate, and a film layer intercepting the invasion of bacteria and alien substances into the wound. The hydrocolloid dressing absorbs a small amount of exudate from the wound to form a gel, thereby providing a moist and slightly acidic environment for a relatively long term under which damage to the tissue is prevented, and a growth of cells constituting the tissue is promoted. However, the hydrocolloid dressing has disadvantages in that it cannot be used for a wound filler, has poor exudate absorptivity of less than 100 wt %, a gel is attached to the wound when it is replaced with new one or removed to act as a nutrition source promoting the propagation of bacteria, and cannot be applied to the wound oozing a large amount of exudate.

Further, U.S. Pat. Nos. 5,501,661 and 5,489,262 recite a hydrogel dressing which includes a polymer film layer having no permeability and a hydrogel coated on the polymer film layer. In this regard, the polymer film layer functions to prevent the hydrogel from being dehydrated and dried, and the hydrogel layer comes into contact with a surface of a wound to absorb an exudate from the wound and maintain the wound under a humid environment to support the healing of the wound. However, the hydrogel dressing has disadvantages in that it cannot be applied to the wound oozing a large amount of exudate because of its poor moisture vapor transmission rate, and it is destroyed when its swelling is maintained for a relatively long time to cause the maceration of a undamaged portion of the skin around the wound.

Furthermore, U.S. Pat. No. 4,664,662 discloses a hydrophilic polyurethane foam dressing which is structured such that a polyurethane foam is surrounded by a net film having fine holes, thereby well absorbing an exudate. However, the hydrophilic polyurethane foam dressing is disadvantageous in that the net film constituting the hydrophilic polyurethane foam dressing is attached to a regenerated skin tissue due to the fine holes of the net film when it is applied to a wound oozing a large amount of exudate, thereby the exudate is not sufficiently absorbed into the polyurethane foam dressing. Another disadvantage is that the polyurethane foam dressing cannot have various shapes, thus it is difficult to apply the polyurethane foam dressing to the wound with a narrow and deep shape.

To sum up, the above conventional dressings are disadvantageous in that they have poor absorptivity and moisture vapor transmission rate, are firmly attached to the surface of the wound, and have poor physical properties. Other disadvantages are that remaining portions of them are attached to the wound after they are used and separated from the wound, and they cannot be used for a wound filler and not be applied to the wound oozing a large amount of exudate.

DISCLOSURE OF THE INVENTION

Accordingly, the present invention has been made keeping in mind the above problems, such as poor absorptivity and moisture vapor transmission rate, the attachment of a dressing to a wound, poor physical properties, the stagnation of a portion of the dressing in the wound after use of the dressing, and unease of filling the dressing in the wound, occurring in the prior art, and an aspect of the present invention is to provide a polyurethane foam dressing for a wound filler, which is applied to a deep wound oozing a large amount of exudate, easily filled in the wound, and has improved absorptivity, moisture vapor transmission rate, the attachment of the dressing to the wound, and physical properties to efficiently support the healing of the wound, and a method of manufacturing the same.

Additional aspects and/or advantages of the invention will be set forth in part in the description which follows and, in part, will be obvious from the description, or may be learned by practice of the invention.

The above and/or other aspects are achieved by providing a hydrophilic polyurethane foam dressing for a wound filler, which is applied to a burn and a deep wound, comprising a hydrophilic foam including a plurality of open cells with a diameter of 50 to 400 µm, and a plurality of pores with a diameter of 10 to 80 µM.

The above and/or other aspects are achieved by providing a method of manufacturing a hydrophilic polyurethane foam dressing for a wound filler, which is applied to a burn and a deep wound, including mixing and agitating 40 to 75 wt % polyurethane prepolymer, 15 to 45 wt % foaming agent, 5 to 35 wt % crosslinking agent, and 0.5 to 15 wt % additive containing a surfactant, a moisturizing agent, and a pigment, injecting a resulting mixture into a mold, and foaming the resulting mixture in the mold.

Reference should now be made to the drawings, in which the same reference numerals are used throughout the different drawings to designate the same or similar components.

A foam dressing for a wound filler according to the present invention includes a plurality of open cells with a diameter of 50 to 400 µm and a plurality of pores with a diameter of 10 to 80 µm, thereby having relatively high absorptivity and moisture vapor transmission rate, and retending an exudate absorbed from the wound therein to maintain the wound under a humid environment.

In other words, the foam dressing of the present invention comprises a hydrophilic foam including the open cells 1 with a diameter of 50 to 400 µm as shown in the drawings. At this time, the pores 2 with a diameter of 10 to 80 µm are formed on surfaces of walls of the open cells 1. A ratio of the open cells 1 in the foam dressing is 50 to 90%. Accordingly, the foam dressing of the present invention has the relatively high absorptivity and moisture vapor transmission rate, and holds the exudate absorbed from the wound therein to maintain the wound under the humid environment. In addition, the foam dressing is freely deformed according to a shape of the wound, thus being easily filled in the wound. That is to say, because the foam dressing is freely deformed, it is useful to fill the foam dressing into the deep wound and to use as a dressing for a wound filler.

A thickness, a width, and a shape of the foam dressing of the present invention are variously controlled according to the shape of the wound. FIG. 1 is a sectional view of the foam dressing for the wound filler according td the present invention.

Further, it is preferable that the foam dressing of the present invention has a density of 0.1 to 0.4 g/cm³. For example, when the density is more than 0.4 g/cm³, the physical properties of the foam dressing are excellent, but moisture vapor transmission rate of the foam dressing becomes poor. On the other hand, when the density is less than 0.1 g/cm³, the moisture vapor transmission rate is improved and the physical properties become poor.

Furthermore, the foam dressing of the present invention is selected from the group consisting of polyurethane, polyethylene, a silicone resin, a natural and synthetic rubber, polyglycolic acid, polylactic acid, or a copolymer thereof; a synthetic polymer, such as polyvinyl alcohol and polyvinylpyrolidone; a natural polymer, such as collagen, gelatin, karaya gum, guar gum, hyaluronic acid, sodium alginate, chitin, chitosan, fibrin, and cellulose, or a synthetic polymer derived therefrom; and a mixture thereof.

Preferably, the foam dressing of the present invention is made of polyurethane. The polyurethane foam dressing is characterized in that it has high absorptivity of 500 to 2000 wt % and high moisture vapor transmission rate of 2000 to 5000 g/m²/24 hrs at 35° C. and a relative humidity of 90%, and rapidly absorbs the exudate from the wound. At this time, the polyurethane is produced by reacting one or more kinds of polyetherpolyol, diisocyanate, and a reactant liquid.

In detail, one or more kinds of polyetherpolyol reacts with diisocyanate to produce a polyurethane prepolymer, and 15 to 45 wt % foaming agent, 5 to 35 wt % crosslinking agent, and 0.5 to 15 wt % additive containing a surfactant, a moisturizing agent, and a pigment are then added to 40 to 75 wt % polyurethane prepolymer to produce a mixture. In this regard, the additive may further include a wound healing promoting agent, a release agent, an antibiotic agent, and a cell growing promoting agent. After coated on a release paper, the mixture is freely subjected to a foaming process at room temperatures to form a foam. Preferably, the mixture is subjected to the foaming process while it is injected into a mold. At this time, a temperature of the mold is 20 to 60° C., and the mixture is separated from the mold after 5 to 60 min since it is injected into the mold. The foam dressing is then cut into a desired shape and size. The foaming process of the mixture using the mold is preferable because the foaming process is simple, and foam dressings with various shapes and thicknesses are manufactured through the foaming process using the mold.

Additionally, one to three moles diisocyanate reacts with 0.15 to 0.95 moles polyetherpolyols to produce the polyurethane prepolymer.

Diisocyanate used to produce the polyurethane prepolymer may be selected from the group consisting of isoporone diisocyanate, 2,4-toluenediisocyanate and isomers thereof, diphenylmethane diisocyanate, hexamethylene diisocyanate, lysine diisocyanate, trimethylhexamethylene diisocyanate, 2,2-bis-4'-propane isocyanate, 6-isopropyl-1,3-phenyl diisocyanate, bis(2-isocyanatoethyl)-fumarate, 3,3'-dimethyl-4, 4'-diphenylmethane diisocyanate, 1,6-hexane diisocyanate, 4,4'-biphenylene diisocyanate, 3,3'-dimethylphenylene diisocyanate, p-phenylene diisocyanate, m-phenylene diisocyanate, 1,5-naphthalene diisocyanate, 1,4-xylene diisocyanate, and 1,3-xylene diisocyanate. Preferably, diisocyanate may be selected from the group consisting of diphenylmethane diisocyanate, 2,4-toluene diisocyanate and isomers thereof p-phenylene diisocyanate, isoporone diisocyanate, and hexamethylene diisocyanate. Examples of polyetherpolyols may include an ethylene oxide/propylene oxide random copolymer with a molecular weight of 3000 to 6000 having three or more hydroxyl groups and an ethylene oxide content of 50 to 80%, and polypropylene glycol with the molecular weight of 1000 to 4000 having two or more hydroxyl groups, mixed with each other in a weight ratio of 30:70. However, it is preferable that polyetherpolyol includes only the ethylene Oxide/propylene oxide random copolymer with the molecular weight of 3000 to 6000 having the three or more hydroxyl groups and the ethylene oxide content of 50 to 90%.

Further, chlorofluorocarbon (CFC-141 b), methylene chloride, or distilled water may be used as a foaming agent. Preferably, distilled water is used as the foaming agent.

Furthermore, a compound with two or more hydroxyl groups may be used as the crosslinking agent. In this respect, examples of the crosslinking agent include 1,3-butanediol, 1,4-butanediol, 1,5-pentanediol, 1,6-hexanediol, neopentyl glycol, propylene glycol, ethylene glycol, polyethylene glycol with a molecular weight of 200 to 2000, glycerol, trimethylolethane, trimethylolpropane, pentaerythritol, sorbose, sorbitol, and a mixture thereof Preferably, glycerol, sorbitol, polyethylene glycol with the molecular weight of 200 to 2000, or trimethylolpropane may be used as the crosslinking agent.

Examples of the surfactant used as the additive include an ethylene oxide/propylene oxide block copolymer selected from the group consisting of L-62, L-64, P-84, P-85, P-105, F-68, F-87, F-88, F-108, F-127, and a mixture thereof manufactured by BASF Co. in Germany, and a silicon-based surfactant selected from the group consisting of L-508, L-5305, L-5302, and L-3150 manufactured by Osi Co. Additionally, the moisturizing agent and wound healing promoting agent are selected from the group consisting of hyaluronic acid, keratan, collagen, dermatan sulfate, heparin, heparan sulfate, sodium alginate, pectin, xanthan gum, guar gum, karaya gum, sodium carboxymethylcellulose, chondroitin sulfate, 3-aminopropyldihydrogen phosphate, chitin, chitosan, gelatin, locost bin gum, and oligosaccharides thereof and a mixture thereof.

BRIEF DESCRIPTION OF THE DRAWINGS

The above and other aspects, features and other advantages of the present invention will be more clearly understood from the following detailed description taken in conjunction with the accompanying drawings, in which.

BEST MODE FOR CARRYING OUT THE INVENTION

Figure 1:
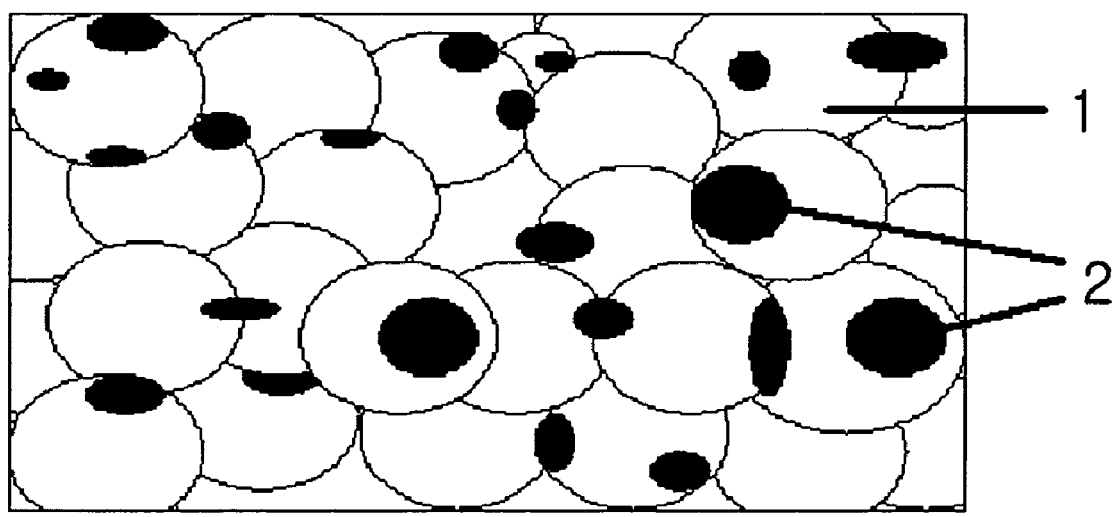
FIG. 1 is a sectional view of a polyurethane foam dressing for a wound filler according to the present invention.

A better understanding of the present invention may be obtained by reading the following examples which are set forth to illustrate, but are not to be construed to limit the present invention.

PREPARATION EXAMPLE 1

After 242.8 g of toluene diisocyanate (TDI) was charged in a 3 l round-bottom flask with a stirrer and heated to 60° C., 1257.5 g of TR-705 (manufactured by Korea Polyol Co.) consisting of an ethylene oxide/propylene oxide random copolymer having three hydroxyl groups and an ethylene oxide content of 75% was added into the round-bottom flask little by little to react toluene diisocyanate with TR-705 for seven hours until a theoretical NCO % was accomplished to produce a polyurethane prepolymer with isocyanate end groups. At an intermediate step of the reaction, a mixture of toluene diisocyanate and TR-705 was sampled to measure NCO % using an n-butyl amine standard solution according to a titrimetry method.

Example 1

After 26.7 wt % distilled water as a foaming agent, 6.4 wt % guar gum as a moisturizing agent, 14.1 wt % glycerine as a crosslinking agent, and 1.4 wt % L-64 (manufactured by BASF CO.) as a surfactant were added to 51.4 wt % polyurethane prepolymer produced in preparation example 1, the resulting mixture was agitated at 4000 rpm for 5 sec, injected into a mold with a predetermined shape and subjected to a foaming process to produce a hydrophilic polyurethane foam dressing. At this time, the mold was 25° C., and the polyurethane foam dressing was separated from the mold after 10 min since the resulting mixture was injected into the mold. A skin layer of the polyurethane foam dressing was removed and cut into pieces with a thickness of 5 mm using a horizontal cutter. The resulting polyurethane foam dressing was 0.24 g/cm$^3$ in terms of density.

The physical properties of the hydrophilic polyurethane foam dressing were measured according to the following methods, and the results are described in Table 1.

(1) Mechanical Properties (Tensile Strength, Elongation, and Modulus)

The mechanical properties of the hydrophilic polyurethane foam dressing were measured using a tensile tester (Universal test machine, manufactured by Instron CO. in USA) according to JIS-K-6401.

(2) Absorptivity (%) and Retention (%)

After an initial weight (A) of a hydrophilic polyurethane foam dressing sample with a size of 3 cm×3 cm was measured, the foam dressing sample was dipped in distilled water at 25° C. for 24 hours, pulled from the distilled water, wiped using a dustless paper to remove water from a surface of the polyurethane foam dressing sample, and weighed (B). Absorptivity of the polyurethane foam dressing sample was then calculated using the following Equation 1.

$$\text{Absorptivity}(\%) = (B-A)/A \times 100 \qquad \text{Equation 1}$$

Furthermore, a 6 kg weight was put on the polyurethane foam dressing sample (3 cm×3 cm) used in measuring the absorptivity for 20 sec, and taken off the polyurethane foam dressing. The resulting sample was weighed (C), and its retention was calculated using the following Equation 2.

$$\text{Retention}(\%) = (C-A)/A \times 100 \qquad \text{Equation 2}$$

(3) Absorption Rate

After a drop of water fell onto a surface of the sample using a pipette, a time taken until water was completely absorbed into the sample was measured. This procedure was repeated ten times, and an average of ten measured values was defined as an absorption rate of water into the polyurethane foam dressing sample.

(4) Moisture Vapor Transmission Rate

The moisture vapor transmission rate of the polyurethane foam dressing sample was measured using a thermohydrostat according to an ASTM E96-95 (Desiccant method). At this time, a temperature and a relative humidity of the thermohydrostat were 35±1° C. and 90±5%, respectively. The moisture vapor transmission rate was calculated using the following Equation 3.

$$P = A/S$$

$$A = ((a_1 - a_0) + (a_2 - a_1) + (a_3 - a_2))/3 \quad \text{Equation 3}$$

(whererin, P: moisture vapor transmission rate (g/m²/24 hr), A: an average weight of the sample increased for one hour (g), S: a moisture vapor transmission rate area of the sample (m²), and $a_0$, $a_1$, $a_2$, and $a_3$: weights of the sample after one, two, three, and four hours, respectively)

(5) Cell and Pore Size

Generally, absorptivity of an exudate into a polyurethane foam dressing depends on a cell and a pore size of the polyurethane foam dressing as well as the hydrophilic property of the polyurethane foam dressing. In other words, the capillary suction per a specific surface area of the polyurethane foam dressing depends on the cell and pore size of the polyurethane foam dressing, thus the cell and pore size of the polyurethane foam dressing affect the absorptivity of the exudate into the polyurethane foam dressing. The cell and pore size of the polyurethane foam dressing may be measured according to a mercury intrusion porosimetry method, but it is preferable to measure the cell and pore size of the polyurethane foam dressing using a scanning electron microscope (SEM). In the present invention, the cell and pore size of the hydrophilic polyurethane foam dressing were measured using the SEM.

(6) Vertical Wicking Performance

Another absorbing ability of the polyurethane foam dressing relates to an ability capable of rapidly transporting the exudate from a wound into the foam dressing. In this respect, a vertical wicking performance is a measure indicating an ability capable of transporting the exudate in an opposite direction against the gravity. Furthermore, a vertical wicking rate and a vertical wicking absorbent capacity pertain to the vertical wicking performance.

1) Vertical Wicking Rate

After a foam dressing sample with a size of 2 cm×20 cm was partially dipped in distilled water at 37° C. containing dyes, a time taken until the foam dressing sample drew water to a position of 5 cm from a surface of water was measured. This procedure was repeated five times, and an average value of five measured values was calculated as the vertical wicking rate.

2) Vertical Wicking Absorbent Capacity

The vertical wicking absorbent capacity was simultaneously measured in conjunction with the vertical wicking rate. The hydrophilic foam dressing sample with a size of 2 cm×20 cm was partially dipped in distilled water at 37° C., and left until the hydrophilic foam dressing sample sufficiently drew water. After the absorption of water into the hydrophilic foam dressing sample reaches an equilibrium state, a height of water absorbed into the hydrophilic foam dressing sample was measured. This procedure was repeated five times, and an average value of five measured values was calculated as the vertical wicking absorbent capacity.

Example 2

The procedure of example 1 was repeated except that 0.4 wt % F-127 (manufactured by BASF Co.) and 1.0 wt % L-64 were added as a surfactant to a polyurethane prepolymer to produce a hydrophilic polyurethane foam dressing. The physical properties of the hydrophilic polyurethane foam dressing were measured in the same manner as example 1, and the results are described in Table 1.

Example 3

The procedure of example 1 was repeated except that 1.0 wt % F-127 (manufactured by BASF Co.) and 0.4 wt % L-64 were added as a surfactant to a polyurethane prepolymer to produce a hydrophilic polyurethane foam dressing. The physical properties of the hydrophilic polyurethane foam dressing were measured in the same manner as example 1, and the results are described in Table 1.

Example 4

The procedure of example 1 was repeated except that 1.4 wt % F-127 (manufactured by BASF Co.) was added as a surfactant to a polyurethane prepolymer to produce a hydrophilic polyurethane foam dressing. Physical properties of the hydrophilic polyurethane foam dressing were measured in the same manner as example 1, and the results are described in Table 1.

Example 5

The procedure of example 2 was repeated except that a raw material was injected in a more amount than example 2 into a mold to increase a density of a hydrophilic polyurethane foam dressing to 0.27 g/cm³. The physical properties of the hydrophilic polyurethane foam dressing were measured in the same manner as example 1, and the results are described in Table 1.

Example 6

After 26.7 wt % distilled water as a foaming agent, 6.4 wt % guar gum as a moisturizing agent, 14.1 wt % glycerine as a crosslinking agent, and 0.4 wt % F-127 (manufactured by BASF CO.) and 1.0 wt % L-64 as a surfactant were added to 51.4 wt % polyurethane prepolymer produced in preparation example 1, the resulting mixture was agitated at 4000 rpm for 5 sec. The agitated mixture was poured on a release paper, coated in a thickness of 2 mm on the release paper using a stainless knife, and subjected to a foaming process at room temperatures to produce a foam. The foam was cut into pieces with a thickness of 5 mm using a horizontal cutter to produce the resulting hydrophilic polyurethane foam dressing. The resulting hydrophilic polyurethane foam dressing was 0.12 g/cm³ in terms of density. The physical properties of the hydrophilic polyurethane foam dressing were measured in the same manner as example 1, and the results are described in Table 1.

Comparative Example 1

A commercial sterilized gauze (commercial name: "sterilized gauze") manufactured by D Co. in Korea was used to compare hydrophilic polyurethane foam dressings according to examples therewith. The physical properties of the commercial sterilized gauze were measured in the same manner as example 1, and the results are described in Table 1.

Comparative Example 2

A commercial polyurethane foam dressing (commercial name: "Allevyn") manufactured by S Co. was used to compare hydrophilic polyurethane foam dressings according to examples therewith. The physical properties of the commercial polyurethane foam dressing were measured in the same manner as example 1, and the results are described in Table 1.

Comparative Example 3

A commercial alginate woven-fabric type of dressing (commercial name: "Curasorb") manufactured by K Co. was used to compare hydrophilic polyurethane foam dressings according to examples therewith. The physical properties of the commercial alginate woven-fabric type of dressing were measured in the same manner as example 1, and the results are described in Table 1.

the sample of example 5 is compared to the sample with the relatively low density of 0.24 g/cm³ of example 2. When the density is increased, the physical properties of the polyurethane foam dressing are not changed, the moisture vapor transmission rate is slightly reduced, and 100% modulus is slightly increased.

In the case of example 6, the cell and pore size are increased, but the density is greatly reduced. Additionally, a shape of the spherical cell is distorted, and the vertical wicking rate and absorbent capacity are reduced.

As for comparative example 1, the gauze dressing is used as a dressing for a wound filler. The gauze dressing has an excessively high moisture vapor transmission rate, thus it

TABLE 1

Physical properties of hydrophilic polyurethane foam dressing

| | | | | Absorption | | [6]Perform. | | | | |
|---|---|---|---|---|---|---|---|---|---|---|
| | [1]D. | [2]C. | [3]P. | [4]Ab. | [5]H. | [7]R. | [8]C. | [9]A. | [10]M. | [11]Tr. |
| E. 1 | 0.24 | 150 | 20 | 1000 | 350 | 2 | 8.2 | 8 | 0.09 | 2800 |
| E. 2 | 0.24 | 200 | 35 | 1000 | 290 | 2 | 7.6 | 3 | 0.09 | 3300 |
| E. 3 | 0.24 | 280 | 65 | 1100 | 260 | 3 | 6.8 | 2 | 0.09 | 3500 |
| E. 4 | 0.24 | 380 | 80 | 1100 | 230 | 3 | 6.5 | 1 | 0.09 | 3800 |
| E. 5 | 0.27 | 220 | 50 | 1050 | 280 | 3 | 7.6 | 3 | 0.12 | 2800 |
| E. 6 | 0.12 | 550 | 280 | 1000 | 150 | 15 | 5.5 | 1 | 0.05 | 4500 |
| C. 1 | 0.11 | — | — | 350 | 70 | 5 | 6.7 | 1 | 0.25 | 6900 |
| C. 2 | 0.14 | 600 | 300 | 530 | 120 | 30* (2 cm) | 3.0* | 150 | 0.12 | 800 |
| C. 3 | 0.01 | — | — | 1000 | 180 | 4 | 6.5 | 1 | 0.03 | 4200 |

[1]D.: Density (g/cm³)
[2]C.: Average open cell size (μm)
[3]P.: Average pore size (μm)
[4]Ab.: Absorptivity (%)
[5]H.: Retention (%)
[6]Perform.: Vertical wicking performance
[7]R.: Vertical wicking rate (min)
[8]C.: Vertical wicking absorbent capacity (cm)
[9]A.: Absorption rate of a drop of water into the polyurethane foam dressing (sec)
[10]M.: 100% modulus (kgf/mm²)
[11]Tr.: Moisture vapor transmission rate (g/m²/hr)
*In the case of comparative example 2, the vertical wicking speed and absorbent capacity were poor 30 min and 2 cm, respectively From the Table 1, it can be seen that in the case of examples 1 to 4, the composition change of surfactants with different hydrophile-lipophile balance (HLB) values leads to the change of the cell and pore size of the polyurethane foam dressing. When a composition of a surfactant with the relatively large HLB value is increased, the cell and pore size are increased. Additionally, larger cell and pore size bring about an increase of an absorption rate of water into the polyurethane foam dressing, but lead to the poor absorption of water into the polyurethane foam dressing in the opposite direction against the gravity (vertical wicking absorption capacity) and poor retention of water in the polyurethane foam dressing. On the other hand, the smaller the cell and pore size are, the higher the vertical wicking absorbent capacity and retention are but the slower the absorption rate of water into the polyurethane foam dressing is.

Figure 2:
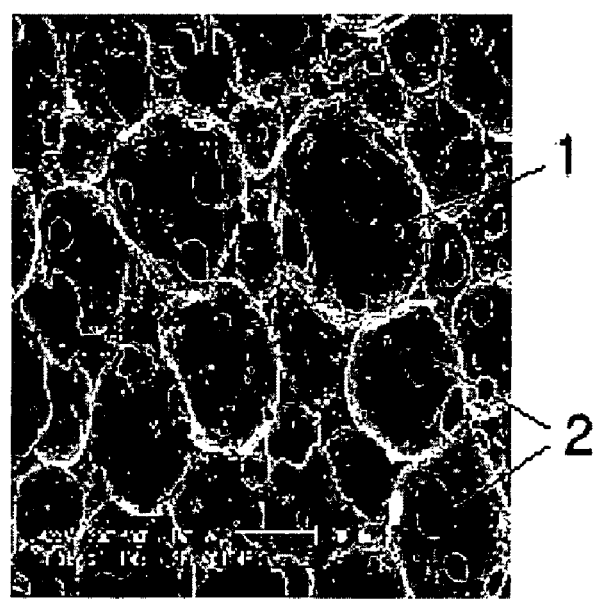
FIG. 2 is a SEM (scanning electron microscope) picture of the polyurethane foam dressing for the wound filler according to the present invention.

FIG. 2 is a SEM picture of the polyurethane foam dressing for the wound filler according to the present invention. In this regard, an average open cell size useful to absorb the exudate is about 600 μm or less, and preferably 50 to 400 μm. Additionally, an average pore size is about 100 μm or less, and preferably 10 to 80 μm.

In example 5, a raw material is injected in a more amount than example 2 into a mold to increase a density of the hydrophilic polyurethane foam dressing to 0.27 g/cm³, and cannot maintain a wound under a humid environment. Additionally, the gauze dressing has much lower absorptivity and retention than the dressing according to the present invention.

In comparative example 2, use of three-layer polyurethane foam dressing leads to much poorer absorptivity, retention, and vertical wicking performance than the hydrophilic polyurethane foam dressing according to the present invention.

In the case of comparative example 3, the alginate dressing mostly used for a deep wound has relatively low 100% modulus of 0.03 kgf/mm², and is swollen after absorbing water to be refigured in terms of its shape. On the other hand, the hydrophilic foam dressing according to the present invention has 100% modulus of 0.09 to 0.12 kgf/mm² before it absorbs water, and the 100% modulus of 0.03 to 0.07 kgf/mm² after it absorbs water. Accordingly, in the case of the hydrophilic foam dressing according to the present invention, it can be seen that the 100% modulus change is slight before and after the hydrophilic foam dressing absorbs water. Furthermore, because the hydrophilic polyurethane foam dressing of the present invention has 20 to 30 times higher density than that of comparative example 3, the dressing of the present invention absorbs about 20 to 30 times more amount of exudate than the alginate dressing of comparative example 3.

INDUSTRIAL APPLICABILITY

As apparent from the above description, the present invention provides a hydrophilic polyurethane foam dressing for a wound filler, which includes a hydrophilic polyurethane foam having a plurality of open cells with a diameter of 50 to 400 µm and a plurality of pores with a diameter of 10 to 80 µm. The hydrophilic polyurethane foam dressing has relatively a high moisture vapor transmission rate, absorptivity, and absorption rate, and is not directly attached to a wound. Additionally, after the hydrophilic polyurethane foam dressing absorbs an exudate, its physical properties are rarely changed, thus it does not leave a portion thereof in the wound. Further, it retends the exudate absorbed from the wound to maintain the wound under a humid environment to support the healing of the wound. Furthermore, because the hydrophilic polyurethane foam dressing is cut in a desired shape after it is subjected to a foaming process in a mold, it may have various shapes and thicknesses, thereby being applied to various wounds.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A hydrophilic polyurethane foam dressing comprised of a plurality of open cells and pores, characterized in that said dressing is a filling type of foam dressing which is filled into the deep wound and then used as a wound filler and has a density of 0.1 to 0.32 g/cm$^3$, an absorptivity of 500 to 2000 wt %, a moisture vapor transmission rate of 2000 to 5000 g/m$^2$/24 hours at 35° C. and a humidity of 90%, the average diameter of said open cells is 80 to 400 µM and the average diameter of said pores is 30 to 80 µm.

2. A method of manufacturing a hydrophilic polyurethane foam dressing comprised of a plurality of open cells and pores, including:

mixing and agitating 40 to 75 wt % polyurethane prepolymer, 15 to 45 wt % foaming agent, 5 to 35 wt % crosslinking agent, and 0.5 to 15 wt % additive containing a surfactant, a moisturizing agent, and a pigment;

injecting a resulting mixture into a mold; and foaming the resulting mixture in the mold to produce a hydrophilic polyurethane dressing having a density of 0.1 to 0.32 g/cm$^3$, an absorptivity of 500 to 2000 wt %, a moisture vapor transmission rate of 2000 to 5000 g/m$^2$/24 hours at 35° C. and a humidity of 90%, the average diameter of said open cells being 80 to 400 µm and the average diameter of said pores being 30 to 80 µm.

* * * * *